United States Patent
Lund et al.

(10) Patent No.: US 6,688,180 B1
(45) Date of Patent: Feb. 10, 2004

(54) MULTI-TEST ASSEMBLY FOR EVALUATING, DETECTING AND MOUNTORING PROCESSES AT ELEVATED PRESSURE

(75) Inventors: Are Lund, Trondheim (NO); Duncan E. Akporiaye, Oslo (NO); Davoud Tayebi, Trondheim (NO); Rune Wendelbo, Oslo (NO); Kai W. Hjarbo, Ranheim (NO); Arne Karlsson, Oslo (NO); Ivar Martin Dahl, Oslo (NO)

(73) Assignee: Sinvent AS, Trondheim (NO)

( * ) Notice: Subject to any disclaimer, the term of this patent is extended or adjusted under 35 U.S.C. 154(b) by 0 days.

(21) Appl. No.: 09/610,423

(22) Filed: Jul. 5, 2000

(30) Foreign Application Priority Data

Jul. 5, 1999 (NO) .......................... 1999 3318

(51) Int. Cl.[7] ............................. G01L 19/04
(52) U.S. Cl. ........................................ 73/708
(58) Field of Search .................. 73/708, 866, 437, 73/64.41, 864.81; 422/99, 101, 63, 64; 210/137; 435/287.2; 429/50, 101, 56; 340/614; 436/147; 250/484.4; 428/545; 264/45.3

(56) References Cited

U.S. PATENT DOCUMENTS

| | | | | |
|---|---|---|---|---|
| 3,994,164 A | * | 11/1976 | Regenass et al. | ......... 73/190 R |
| 4,820,597 A | * | 4/1989 | Lim et al. | ...................... 429/50 |
| 5,466,608 A | * | 11/1995 | Lapluye et al. | ............... 436/86 |
| 5,869,750 A | * | 2/1999 | Onan et al. | ................ 73/64.41 |
| 5,939,312 A | | 8/1999 | Baier et al. | |
| 6,117,334 A | * | 9/2000 | Coury et al. | ................. 210/739 |
| 6,238,929 B1 | * | 5/2001 | Antonenko et al. | ......... 436/180 |
| 6,241,378 B1 | * | 6/2001 | Amberg et al. | .......... 366/152.4 |
| 6,258,323 B1 | * | 7/2001 | Hormann et al. | ............. 422/99 |

FOREIGN PATENT DOCUMENTS

| | | |
|---|---|---|
| DE | 19736641 | 3/1999 |
| EP | 0635713 A1 | 1/1995 |
| WO | 95/12608 | 5/1995 |
| WO | 96/11878 | 4/1996 |
| WO | 98-36826 | 8/1998 |
| WO | 98/57181 | 12/1998 |
| WO | 99/30817 | 6/1999 |

* cited by examiner

*Primary Examiner*—Edward Lefkowitz
*Assistant Examiner*—Octavia Davis
(74) *Attorney, Agent, or Firm*—Wenderoth, Lind & Ponack, L.L.P.

(57) ABSTRACT

A multi-test assembly for evaluating, detecting and monitoring processes at elevated pressure is described. The Mufti-test assembly has a pressure vessel equipped with trays or plates with a multitude of individual test cells, an optional lid for sealing the cells, and a system for the detection and/or monitoring of the processes in each individual test cell, in situ. Uses of the invention are detection of solid structure formation or phase transformation in, for example, hydrocarbon systems or mixtures of hydrocarbon and water, and also in an automated test which is optimized simultaneously with regard to several test parameters in the testing of inhibitors for gas hydrate formation. The multi-test assembly has built-in systems for pressure and temperature control. The assembly may also be connected to a set-up for the automatic dosing of reagents.

15 Claims, 11 Drawing Sheets

MULTI-TEST ASSEMBLY FOR EVALUATING, DETECTING AND MOUNTORING PROCESSES AT ELEVATED PRESSURE

FIELD OF THE INVENTION

The present invention relates to a multi-test assembly for evaluating, detecting and monitoring processes at elevated pressure, and uses of the mufti-test assembly. Further, the present invention relates to a system for fast, systematic and effective testing and detection of solids formation such as those used for testing and optimizing of chemicals for controlling gas hydrates.

BACKGROUND OF THE INVENTION

One of the most challenging problems in oil and gas exploration is the presence of natural gas hydrates in transport pipelines and equipment. Natural gas hydrate is an ice-like compound consisting of light hydrocarbon molecules encapsulated in an otherwise unstable water crystal structure. These hydrates form at high pressures and low temperatures wherever a suitable gas and free water are present. Gas hydrate crystals can become deposited on pipeline walls and in equipment, and in the worst case, lead to complete plugging of the system. Costly and time-consuming procedures may be needed to restore flow again. In addition to the economic consequences, there are also numerous hazards connected to hydrate formation and removal. Although gas hydrates are generally thought of as a problem mostly in connection with gas production, they are also a significant problem for condensate and oil production systems.

To control gas hydrates, the usual approach has been to take steps to avoid any hydrate formation at all. This can be achieved by keeping pressure low (often not possible from flow or operational considerations), keeping temperature high (usually by insulating), removing the water completely (costly equipment and difficult), or by adding chemicals that suppress hydrate formation thermodynamically or kinetically. Insulation is very often used, but is not sufficient alone. Adding chemicals, specifically methanol (MeOH) or ethylene glycol (EG), is therefore the most widespread hydrate control mechanism in the industry today (E. D. Sloan Jr., Clathrate Hydrates of Natural Gases, Marcel Dekker, Inc., New York, 1998, pp. 164–170). These antifreezes ,expand the pressure-temperature-area of safe operation, but are needed in large quantities—50% of the water liquid fraction is not unusual in water-rich production. The use of MeOH in the North Sea may approach 3 kg per 1000 Sm3 of gas extracted. The need for such large amounts of antifreeze places severe demands on logistics of transportation, storage and injection in offshore facilities with a deficiency of space.

Inhibitor chemicals of different types are not only used in pipeline transport and processing areas, but also extensively in drilling operations and wells.

Mainly due to the huge amounts and large costs involved in using traditional inhibitors like MeOH, there has ver the last decade been extensive efforts devoted to finding chemicals which may be effective at controlling hydrates at much lower concentrations.

Many oil companies and research institutes have contributed to this effort, and at present, the results are divided into three main categories; kinetic inhibitors, dispersants, and modificators. Kinetic inhibitors have: an affinity for the crystal surface, and thereby can be used to prevent hydrate crystal growth. Dispersants act as emulsifiers, dispersing water as small droplets in the hydrocarbon liquid phase. This limits the possibilities for hydrate particles to grow large or to accumulate. The modifiers act as a combination of the two other methods, attaching to the crystal surface, the hydrate is dispersed as small particles in the hydrocarbon liquid phase.

Dispersant and modifiers are generally dedicated for condensate and oil production systems.

The development of low dosage chemicals for hydrate control has been somewhat successful, although there are practical and environmental drawbacks to most of them.

One principal reason for the limited success has been the lack of a method and a system for fast systematic and effective testing of large test matrixes for new chemicals. Most of these chemicals work efficiently only in blends. Further, the blends have to be suited to each field fluid which may contain other field chemicals such as corrosion, wax, and scale inhibitors.

The present invention will also definitely affect testing and optimizing of other field chemicals (e.g. corrosion, wax and scale inhibitors). Not necessarily used in the same amount per volume unit pipe as the hydrate inhibitors, the total amount of chemicals (sometimes with environmentally highly adverse effects) are huge, as they are used in such a great number of pipelines.

The present invention provides a method for fast, systematic and effective detection and monitoring of phase transformation or solids formation such as those used for multi-testing of chemicals for controlling gas hydrates.

Many compounds, such as, for example, gas hydrates, are formed in liquids, or in mixtures of liquids and gases under elevated pressures. For testing and studying their formation, it is necessary to use pressure vessels. The pressure vessel has to be designed such that the handling of it does not represent any unnecessary hazard, provided it is used according to working instructions.

Pressure cells used for testing of gas hydrate formation are described in E. D. Sloan Jr., Clathrate Hydrates of Natural Gases, Marcel Dekker, Inc., New York, 1998, pp. 292–300. A test cell (15–300 cc) usually consists of a sight glass for visual confirmation of hydrate formation and disappearance. Normally only up to 50 per cent of the cell volume is liquids, with the remainder being gas and hydrate. The cell is enclosed in a thermostated bath with thermocouples in the cell interior to measure the thermal lag between the cell and the bath. The pressure in the cell is usually measured via Bourdon tube gages or transducers. Mixing in the cell may be provided by mechanical or magnetic agitators, by rotating or rocking the cell, by bubbling gas through the liquids, or by ultrasonic agitation. Hydrate formation is normally tested in one of three modes: isothermal (constant temperature), isobaric (constant pressure) or isochoric (constant volume). The hydrate is observed visually or detected through measurements of temperature and pressure in the cell, gas consumption, or apparent liquid viscosity.

Common to all test cells mentioned, and for all other known methods for testing of gas hydrate formation on laboratory scale, is that each pressure vessel can only perform one test mixture at the time. When a pressure vessel weights up to 8 kg, handling more than a small number of vessels at the time is difficult. This makes each test a very resource intensive process, and there is consequently a great need for more efficiency, rationalization, downscaling and automation.

Common to all the test procedures mentioned and for all other known test procedures for the testing of gas hydrate formation on laboratory scale with the purpose of discovering new inhibitors or to optimize existing inhibitors, is that these are performed in a cumbersome and expensive manner by having to separately prepare each reaction mixture, which typically consists of 4–7 reagents, and by adding the reagents one by one. Furthermore, each reaction mixture is typically prepared in batches of 5 to 100 g and tested in expensive and heavy pressure vessels with internal volumes often in the range of 25 to 250 ml and with weights of up to 8 kg per pressure vessel, causing considerable expense due to a large consumption of often expensive reagents and due to the fact that the handling of the heavy pressure vessels often makes it difficult to handle more than one pressure vessel at the time. The combination of all these elements are, according to state of the art technology, making each inhibitor test a very resource intensive process. Consequently there is a great need for greater efficiency, rationalization, down-scaling and automation.

In recent years new, automated methods for systematic preparation of new compounds, so-called "combinational techniques", have been developed. In WO 9512608-A1 there is, for instance, a description of an apparatus and a method for a) the synthesis of several molecules on substrates, comprising distribution of the substrates in the reaction chambers, b) combination of the first addition of these molecules with different reagents in each of the reaction chambers, c) moving the substrates through tubing to separate mixing chambers where the substrates are mixed, d) redistribution of the substrates by transport through tubing back to the reaction chambers, and e) combination of a portion number two of different composition to the first portions of molecules in the different reaction chambers in order to prepare new mixtures. This publication describes only a system for mixing and distribution of different molecules and not a system for hermetical sealing the reaction chamber, which makes it possible to operate at high pressures, and this system would thus, not be suitable for testing inhibitors. In Patent Application WO 96/11878, there is a description of extensive use of a combinatorial arrangement for synthesis of new materials. Even though this patent application gives a detailed description of instrumentation and equipment developed for different purposes, pressure vessel systems required for performing the tests under the prevailing physical conditions of elevated pressure are not described.

Pressure vessels with several chambers designed for special purposes are known. There is for instance in U.S. Pat. No. 5.505.916 a description of a metal cassette which can be opened and closed like a suitcase, and which has an interior with compartments intended for placement of the different instruments ;used by dentists, where these may be sterilized by autoclaving. Furthermore, there is a series of known equipment intended for synthesis of proteins and bio-polymers, where the design comprises sheets with a large number of chambers intended for screening of synthesis and crystal growth, in its simplest form, as described in U.S. Pat. No. 5,096,676. U.S. Pat. No. 5,400,741 describes a diffusion cell for growth of the largest and the most perfect crystals possible of macromolecular compounds by a technique called the "hanging drop" technique. Several patents, for example, U.S. Pat. Nos. 5.013.531, 5,531,185, 5,362,325 and EP 0.553.539 A1, deal with cells for growth of proteins and bio-polymer crystals in spaceships. Common to the latter patents is that the designs described are very sophisticated and thus very expensive, because they are intended for use in space-vehicles. Common to all equipment designed for test and crystal growth of proteins and bio-polymers is that they are all meant for use at ambient pressures, and that they consequently are not designed to withstand conditions typical for gas hydrate formation. Typical pressures in pipelines are 40–400 bar, but for reservoirs, the pressure may range up to 1000 bar. There is, for example, a design called "multiblock" (Krchnak, V., Vagner, J.; Peptide Res. 3, 182 (1990)) consisting of i) a Teflon block holding 42 reactors, polypropylene syringes equipped with polymer filters, ii) a vacuum adapter connecting each reactor to a vacuum line which enables rapid washing in a not further described apparatus for continuous flow, iii) two Teflon plates with 42 stoppers to which the Teflon block is fastened during use, and iv) a glass cover used during homogenization. The problem with this design is that the reactors, which are made of glass and which do not have protected side walls, may be used only at low pressures.

Large pressure vessels intended, for instance, for the growth of crystals, are known, and examples are described in U.S. Pat. Nos. 5,322,591 and 5,476,635. The purpose of these pressure vessels and similar ones is to make it possible to carry out large-scale synthesis, for which there is a great need in many situations, when a synthesis procedure has been established and scale-up is desired, or when the purpose is to grow single crystals as large as possible.

The only equipment known that can, in part, be used for testing of liquids and gases and mixtures thereof at elevated pressures is described in PCT/NO98/00051, wherein a "multiautoclave for combinatorial synthesis of zeolites and other materials" is disclosed. This multiautoclave has a multitude of chambers where liquids can be introduced, whereafter the chambers are sealed and this equipment might, thus, be used for practical work with combinational testing of inhibitors, in as much as zeolite synthesis requires hydrothermal treatment of a solution or gel with relatively high content of water and often high contents of organic compounds in a closed chamber. With special techniques, gases can also be introduced into the chambers of the multiautoclave disclosed in PCT/NO98/00051, but this would require additional equipment not disclosed in the application unless the atmospheric pressure is sufficient. This multiautoclave also has no means for monitoring or detecting the formation of solid phases in the chambers in situ, under elevated pressure.

An important feature when dealing with a large series of tests is how gas hydrate formation, or more generally, formation of solid phases can be detected or monitored in a rational way in a multitude of test-cells in situ, under pressure, preferably in parallel, without insuperable expense, something which is not described in state of the art technology. As far as is known, this type of work is performed in the same manner by all laboratories engaged in testing of gas hydrate formation and inhibitors for gas hydrate formation.

One of the main goals of the present invention is to develop a complete system for detection of phase transformation or particularly solid structure formation in hydrocarbon systems such as those used for screening of gas hydrate inhibitors. This includes the study of conditions for formation of gas hydrates and other compounds formed in hydrocarbons and in mixtures of hydrocarbons and water under elevated pressure in a more cost efficient manner.

It is therefore important to improve a series of cost efficient parameters, such as:

1. Measuring time: the time required for testing and analyzing a certain number of experiments can be considerably reduced using a multi-test cell assembly.

2. Measuring equipment: automated measuring equipment for detection of the changes in each individual test cell in situ.
3. Data sampling: automated data sampling and storage of the detected signals from individual test cells.
4. Data treatment: automated detection and identification of formed solid structures, i.e. based on detected signals from individual test cells, a reference library stored in a database and software that can handle the sampled data and monitor the solid phase formation.
5. Dosing of reagents: a large number of test cells present in one pressure vessel can be connected to an automatic dosing set-up which makes quick and exact additions of all liquids or liquid mixtures, and an analogous system for the dosing of gases, if needed.
6. Operation: simple, fast and easy-to-use mechanism for the closing and opening of the pressure vessel and the individual test cells, including simple cleaning of the individual test cells and the pressure vessel for reuse.

Furthermore, the aim of the invention described here is to design automated equipment for larger test series and for the preparation of formulations based on mixtures of different liquids/solutions and gases with varying ratios.

These and other aims are achieved through the present invention, which represents a break-through in cost reduction for detection and monitoring of, for example, gas hydrate formation.

SUMMARY OF THE INVENTION

In accordance with the object of the invention, there is provided a multi-test assembly for evaluating, detecting and monitoring processes at an elevated pressure, comprising a pressure vessel, means for controlling the temperature and pressure in the pressure vessel, a plurality of test cells organized on one or several trays or plates arranged inside the pressure vessel, means for charging test samples into the test cells before pressurization, and means for detecting and monitoring the content of each individual test cell, in situ.

Preferably, the test cells are lined with a disposable insert or lining. The degree of interaction between the contents of the individual test cells and between the individual test cells and the atmosphere in the pressure vessel is also controllable. The contents of the individual test cells may, therefore, interact fully with the pressure vessel when the test cells are kept open, or there may be no interaction between the contents of the individual test cells when the test cells are kept closed.

Another essential part of the multi-test assembly is a sub-unit for detecting or monitoring the formation of gas hydrates or other phases in hydrocarbons. The changes in each individual test cell are to be automatically detected or monitored and the sampled data are to be stored in a matrix, for example, in a computer and treated separately. The system for detecting or monitoring phase transitions in the closed, pressurized cells is essential for the practical functioning of the multi-test unit. In principle, any system that in a reliable manner can yield relevant information about phase transformations or whatever other reaction or restructuring of matter taking place in the interior of the cells can be used, and for each specific target reaction or class of reactions, the most suitable and cost efficient method of detection or monitoring must be chosen.

In one preferred embodiment, the detecting and monitoring means may comprise a plurality of devices placed on any side of a test cell tray intended to monitor or interact with the contents of the individual test cells. An appropriately shaped magnetic stirrer may be arranged in each test cell for mixing the medium and removing gas-bubbles from the cell walls during operation. Detector means may be arranged outside the test cell wall for sensing the movement of a magnetic stirrer inside the test cell as a measure of the viscosity of the contents in the test cells.

The detecting and monitoring means may in yet another embodiment of the invention comprise optical fiber probes placed in each test cell.

In yet another embodiment, the detecting and monitoring means may comprise a γ-source arranged on one side of the test cell tray(s) and one or several detectors arranged opposite of the γ-source, on the other side of the tray(s).

Detecting and monitoring means may comprise one or more recording devices, such as a video camera, IR camera or optical fibers for observation of visible reactions or other events such as temperature changes, in all test cells simultaneously, and an appropriate marker may then be arranged in each individual test cell giving visible contrast to the image of the recording device. It is also possible to measure the mixture temperature in each individual cell using optical fibers.

The invention also comprises use of the multi-test assembly defined above for detecting solid structure formation or phase transformation in, for example, hydrocarbon systems or mixtures of hydrocarbon and water, and use of the mufti-test assembly, as defined above, for testing of inhibitors for solid structure formation as, for example, gas hydrate formation in hydrocarbon systems or mixtures of hydrocarbon and water.

In many situations, an optical method, such as optical fiber sensors, would be a suitable detection method, for instance, whenever the reaction that takes place in the cell in some way affects the transmission, reflection or dispersion of light or any particular wavelength of light. In a similar manner, other classes of electromagnetic-, X-rays or γ-radiation can be used to detect the phase transformations or reactions. If only one open multi-cell tray is used, one or more video or IR cameras inside or outside of the pressure vessel may be used.

If the phase transformation or the reaction in the cell leads to a change in viscosity, this can be detected by any mechanical device suitable for measuring viscosity directly, for example, by a moving magnetic body inside the cell and a sensing device outside the cell that can sense the movement of the inner body using induced currents in an electrical circuit. If the phase transformation or the reaction taking place in the cell is exothermal or endothermal, the temperature change in the cell wall can easily be monitored, for example, a thermocouple can even be mounted so that it protrudes within the wall so that the temperature in the cell content is monitored directly. Likewise, if the reaction leads to a change in pressure, this can be monitored either by a pressure transducer or other pressure sensor device in the cell or by the in-flux or out-flux of matter, in the case the cell is connected to a reservoir at constant pressure. If the phase transformation or the reaction taking place in the cell leads to a change that affects the propagation of sound in the cell, an acoustic detecting system can be applied. Furthermore, if the phase transformation or the reaction taking place in the cell affects the conductivity of the content, this can easily be monitored, and likewise, sensors that are sensitive to certain ions or gases can be used, such as pH-electrodes or oxygen sensing electrodes in cases when a phase transformation or a reaction leads to a change in pH or oxygen activity in the cell.

In the specific case of gas hydrate formation in mixtures of hydrocarbons and water, many of the above detection systems can be applied, since the phase transformations or the reactions that lead to the formation of gas hydrates affect most of the above mentioned detectable properties of matter. Gas hydrates are white or opaque, whereas gases, water and light hydrocarbon liquids are to a certain degree transparent to light and have different light reflection properties. Thus, any of the above-mentioned optical methods of detection or monitoring can be applied. The formation of gas hydrates is exothermal, and it represents a condensation of matter, since a gaseous component is solidified, so both methods that monitor heat fluxes and pressure changes can be applied. Gas hydrate formation also affects viscosity, so any applicable method for the monitoring of viscosity can, in principle, be applied. Whenever the water-phase consists of salt water, the occlusion of the water in the solid gas hydrates will lead to changes in conductivity. Finally, since gas hydrates are crystalline compounds, they can be detected and monitored by X-ray or gamma-ray-diffraction, provided the cell-design is such that the X-rays or gamma-rays can penetrate the cell walls without loosing too much intensity. In conclusion, since a multitude of methods of detection and monitoring are available, the problem reduces to designing the cells, the pressure vessel and the other accessories in such a way that the experiments can be performed at a lowest possible cost per experiment.

The most important feature of the present invention is the fast and simple operation of the multi-test cells enabling many tests to be conducted at relatively short time, for example, having 10–1000 or more available test cells on one tray, and placing several such trays on top of each other. Automated addition of the ingredients enables quick and exact addition of all liquid or liquid mixtures. In such a system, the mixture of ingredients are brought to react in a volume reduced typically to 1/100 of what is usually used, and thereby achieving a more compact system with reduced consumption of reactants and cheaper tests.

With the present invention it is possible to change the experimental conditions such as pressure, temperature or gas mixture during the experiments, in such a way that:

all experiments are carried out at the same time by having many parallel and relatively small test cells on one or several trays/plates inside the pressure vessel, same gas mixture feeding under the experiments, and same temperature during the experiments.

Applications for the present invention are, in addition to gas hydrate inhibitor testing and other problems related to the production, transportation and storing of hydrocarbons, in any field of activities within research and development and routine testing related to products where at least one production-step comprises the mixing of different liquids, for example, in the fields of organic and inorganic synthesis, paint formulation, emulsions, blending of fuels, food industry, fragrants and flavors, dispersions of powders in liquid or gas, etc. Furthermore, applications within clinical testing, etc., where a liquid or gas is added to a liquid, whenever the aim is to detect/monitor or test for the formation or precipitation of solid phases, crystalline or non-crystalline. The invention is, in particular, aimed at applications where open vessels cannot be used, and more specifically for applications where it is required to operate at elevated pressures. By elevated pressure is meant pressures above 1 bar or above ambient pressure in general. For production of hydrocarbons, pressure regions of interest may typically be in the order of, but not limited to, 50 to 400 bar in production and transportation (pipeline) systems (in some cases the pressure may be higher) and 100 to 1000 bar in hydrocarbon reservoir systems. In hydrocarbon systems, the temperature will typically range from −50° C. to 300° C., but when simulating reservoir conditions the temperature may range from −100° C. to 1000° C.

Crystallization of metals and oxides and other compounds from melts have many important industrial applications. The present equipment can be designed so that it can be used for tough conditions of up to about 1000° C., and for pressures of up to at least 200 bars.

BRIEF DESCRIPTION OF DRAWINGS

Further advantages and characteristic features of the present invention are given in the following description by referring to the drawings which, as mere examples without limitations, show some designs related to this invention.

DETAILED DESCRIPTION OF THE PREFERRED EMBODIMENTS

The multi-test assembly comprises various sub-units combined so that they together serve the purpose of the present invention. The sub-units are a pressure vessel, one or several trays or plates; each with a multitude of test-cells, optionally one or several stirring units, one data sampling unit containing one or several measuring or monitoring units, and one or several parallel data-treatment and interpretation units.

The Pressure Vessel

Figure 1:
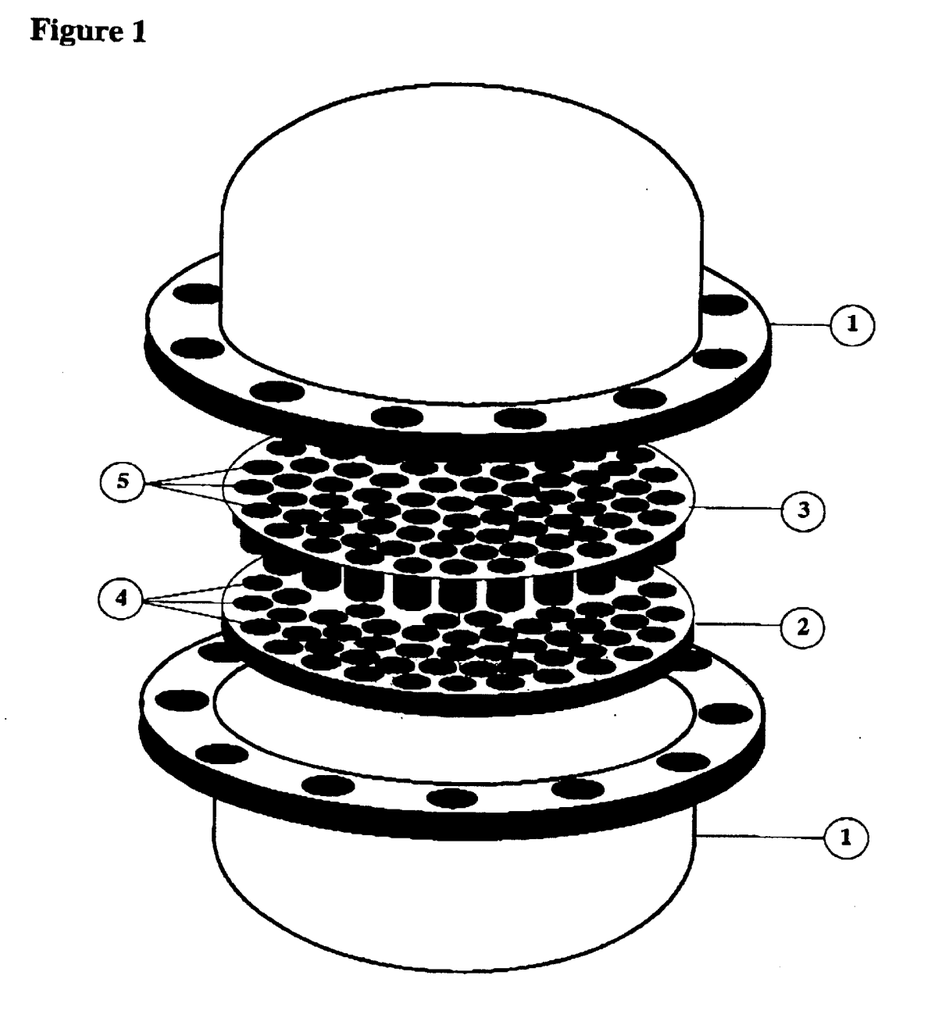
FIG. 1 is an exploded view of an embodiment of the multi-test assembly according to the invention.

FIG. 1 gives a schematic presentation of the multi-test assembly with some of its components disassembled. A pressure vessel 1 consists of two hemispheres or similar shaped parts of tough material with flanges, as illustrated in FIG. 1, which constitute an outer shell of the multi-test assembly. The hemispheres may be of any size or shape and may be placed horizontally or vertically. The pressure vessel may also be made like a closed pipe with hemispherical or plain ends. The two hemispheres are joined tightly together by any suitable means using the flanges and necessary gaskets. The pressure vessel 1 is constructed to be pressure tight and dimensioned such that the degree of deformation that will take place under the operational conditions becomes negligible. Plates or trays 2 with test cells 5 and instrumentation are fitted into the pressured vessel with any needed cables passing through the vessel walls.

The pressure vessel is equipped with any appropriate commercially available means (not shown in the figures) for controlling the temperature and pressure in the pressure vessel.

The Tray with Test Cells

Figure 2:
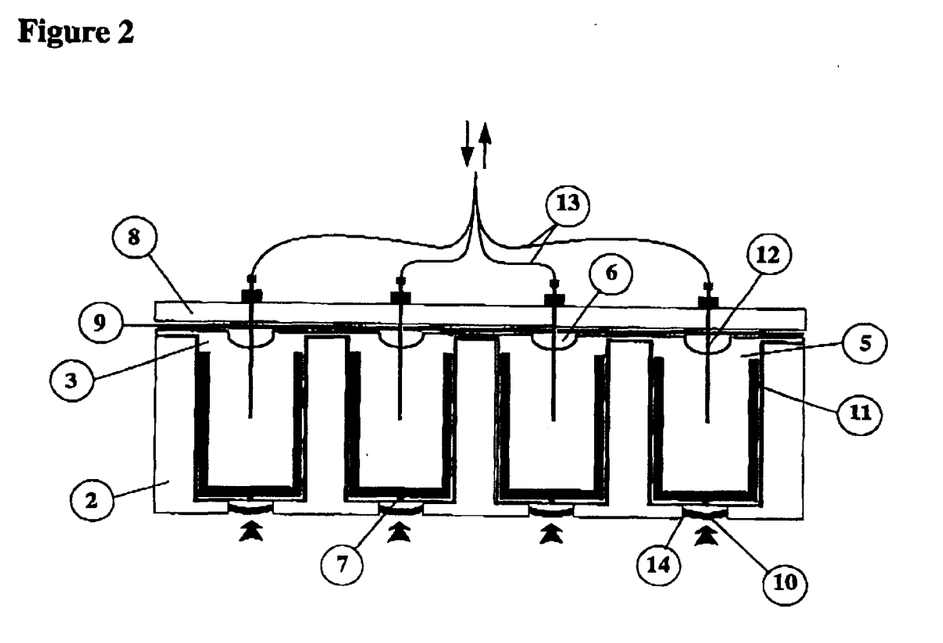
FIG. 2 is a side view of test cells and detecting and monitoring means in the form of fiber optic probes according to an embodiment of the invention.

The pressure vessel contains one or several plates or trays 2 of any shape and thickness made from, for example, metal or plastic. In FIG. 1, trays or plates 2 are fitted horizontally in the middle of the pressure vessel that results when the two hemispheres are joined. Each plate has several or a multitude of wells 4, made as holes in the plate body. Since cleaning and washing of the cells may be critical depending on the chemical used, a thin single-use multi-cell liner 3 can be used for each measurement. The thin liner 3 is shaped so that lined wells 5 are formed in all of the holes 4 in the tray 2, and is fitted onto this tray. The liner is placed in the cell tray 2 before each measurement and can be easily changed after each test by simply removing it from the top of the cell tray 2. The shape of this liner 3 may be such that the incoming gas can enter to it easily from side holes 6 at the top of it, as indicated in FIG. 2. The single-use liner 3 can be put in place and removed in a simple manner so that it can be manipulated by a robot. Testing of gas hydrates will probably require metal walls in the test cells 5 of the liner 3.

The plates or trays 2, optionally lined with thin single use inserts or linings 3 form a matrix of test cells 5 where the tests are taking place. Each tray may have from 10 to 10.000 or more separate test cells. Each test cell has a volume of from 0.02 to 20 ml, typically about 1–2 ml. The thickness of the different plates or trays 2 and the corresponding liners may vary, always keeping in mind that a maximum number of test cells with optimal size is desired. Whenever the differential pressure over a tray is zero, there is no special condition in the choice of material strength. The test-cell diameter could, therefore, be, for example, 10 mm where the cell walls may have a thickness of 0.25–1 mm. Various measuring or control equipment may be cast in the tray to ensure high degree of safety and a compact design.

The individual wells in the tray are optionally covered with a cover means or cover plate 8 as shown in FIG. 2, made, for example, from a light metal, or a thermoplastic or another appropriate material that fulfills the desired measuring conditions and can withstand the action of the chemicals introduced in the test cells under high pressure. The cover means 8 ensures that there is no connection between neighboring cells. The trays and liners are designed such that all the test cells are connected to the same gas phase during the experiments. Above, as part of cover means 8, and/or below the tray 2 with the test cells, there may be placed a tray with devices intended to act on, or monitor the contents of the individual test cells. FIG. 2 illustrates how one tray or plate 2 equipped with a lining insert 3 and a cover plate 8 equipped with fiber optic probes 13 are mounted on top of each other in a modular manner. The fiber optical probes 13 may be fixed in the cover plate 8, thus, all probes can be set on place or removed by one operation. To ease the cleaning procedure, a thin single use foil 9 may be used between the cells and the cover means. This foil is changed after each test. Depending on the desired measuring conditions, open or closed test-cells may be applied. Several trays with test cells may be placed in a pressure vessel containing the same gas mixture temperature and pressure while the liquid mixtures in the test cells could be different.

A large number of test cells present in one pressure vessel can be connected to a commercially available automatic dosing set-up 100 which makes a quick and exact addition of all liquids or liquid mixtures, and an analogous system for the dosing of gases if needed.

The Stirring Units

Figure 3:
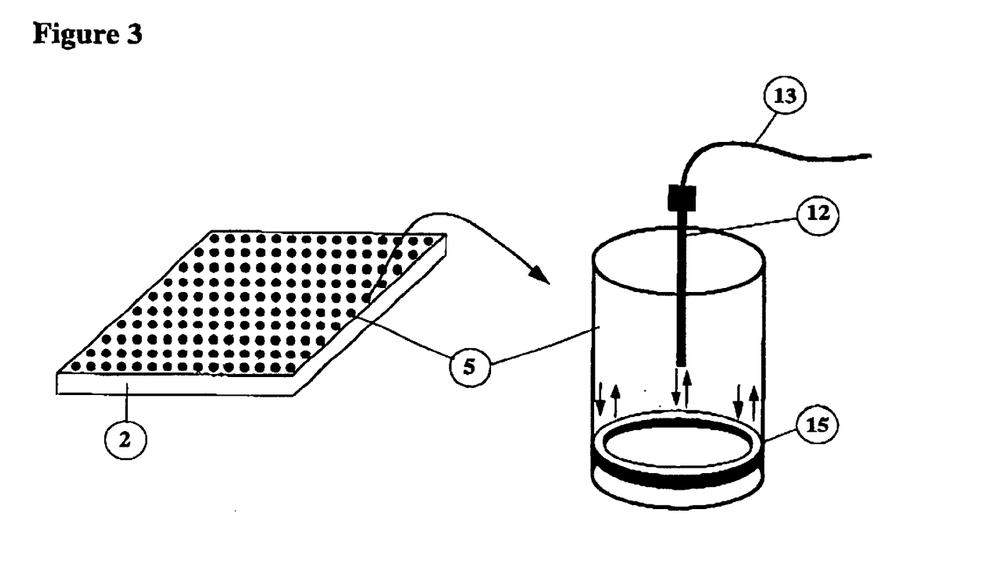
FIG. 3 shows a tray with a multitude of test cells and an individual test cell with fiber optic probe detecting means and a U-shaped magnetic mixer according to one embodiment of the invention.

For mixing of the medium and removing gas bubbles from the cell walls, a U-shaped magnet mixer 11, or a ring-shaped magnet mixer 15 or any other suitable mixing device, is placed in each cell. The U-shaped magnet mixer 11 rotates around its vertical axis when it is exposed to an external magnetic field. A sphere is used at the bottom of the U-magnet to reduce the friction and achieve a smooth rotation. The ring-shaped magnet mixer 15 is pulled up and down in the cell by a magnetic field as illustrated in FIG. 3. The magnets may by washed after each experiment.

Figure 5:
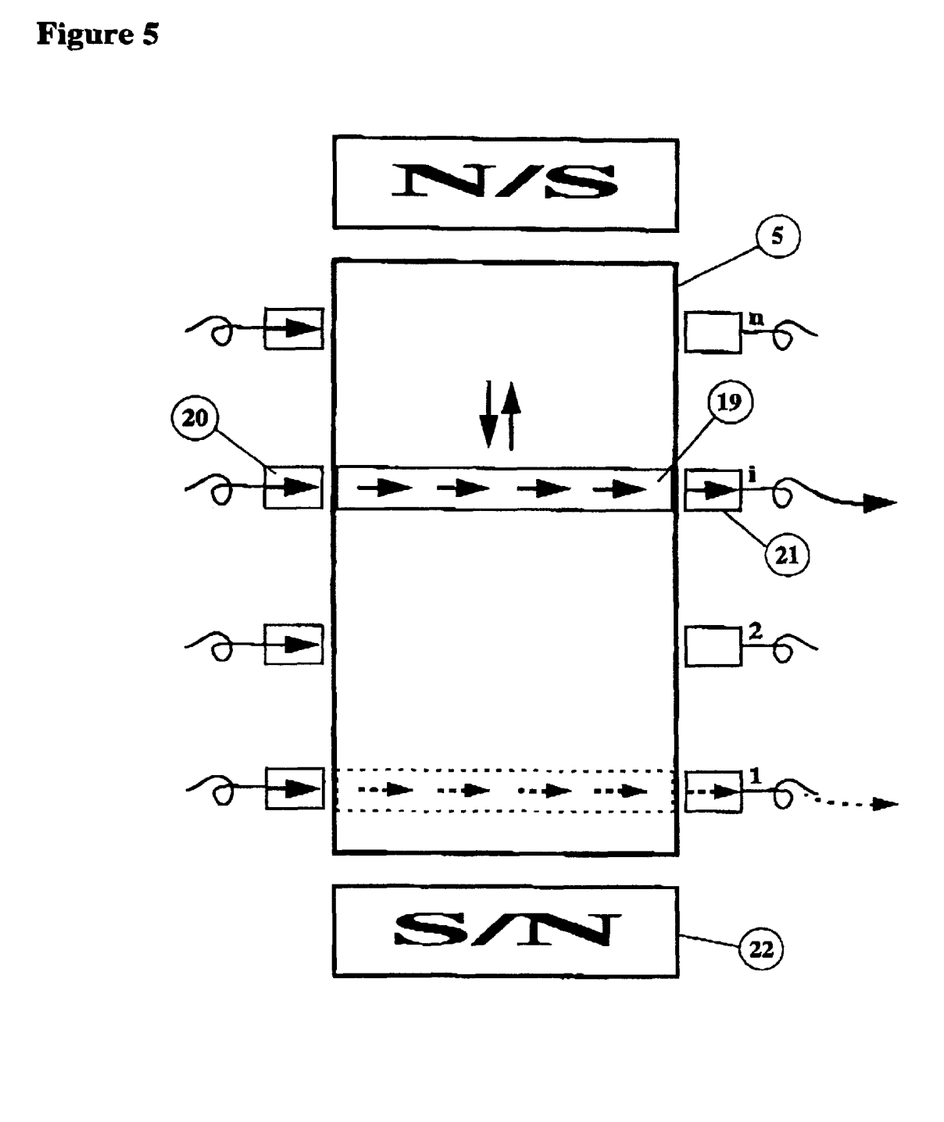
FIG. 5 illustrates a principle for detecting the movement and/or position of a magnetic stirrer in a test cell according to an embodiment of the invention.

Equipment for generating a variable magnetic field in each cell may be integrated in the cell plate, as illustrated in FIG. 5, or be made by another plate fitted above or below the plate with the test cells. This second plate may be fitted with any equipment used for activating, controlling or monitoring externally certain conditions of the content in the cells.

The Detection/Monitoring System

In one preferred embodiment, the detection system is based on the application of optical fibers. Since the reflected or transmitted light intensity is a function of concentration of solid structures in front of the probe, the detected light intensity from the probe measuring volume can be used to detect the formation of solids in the medium. The local solids concentration is then determined based on measured light intensity. The rate of solids growth is obtained based on the changes in the detected light intensity using a proper calibration function.

FIG. 2 illustrates the side view of a section in a mufti-cell test system where one optical fiber probe 12 is placed in each cell 5. The multi-cell test assembly consists mainly of one or several trays, boards or containers 2 of any size and shape with a certain number of test-cells and corresponding optical fibers, as shown in FIGS. 2 and 3. The tray is a board made of a light metal such as aluminium or hard plastic or any other suitable material containing a certain number of cells being open in both ends. A one-way membrane 10 may be used to cover a bottom cell hole 14, ensuring only inflow of hydrocarbon gas to level the pressure inside and outside the cell. The signal from each probe 13 is collected, stored and treated either parallel or sequentially.

Figure 4:
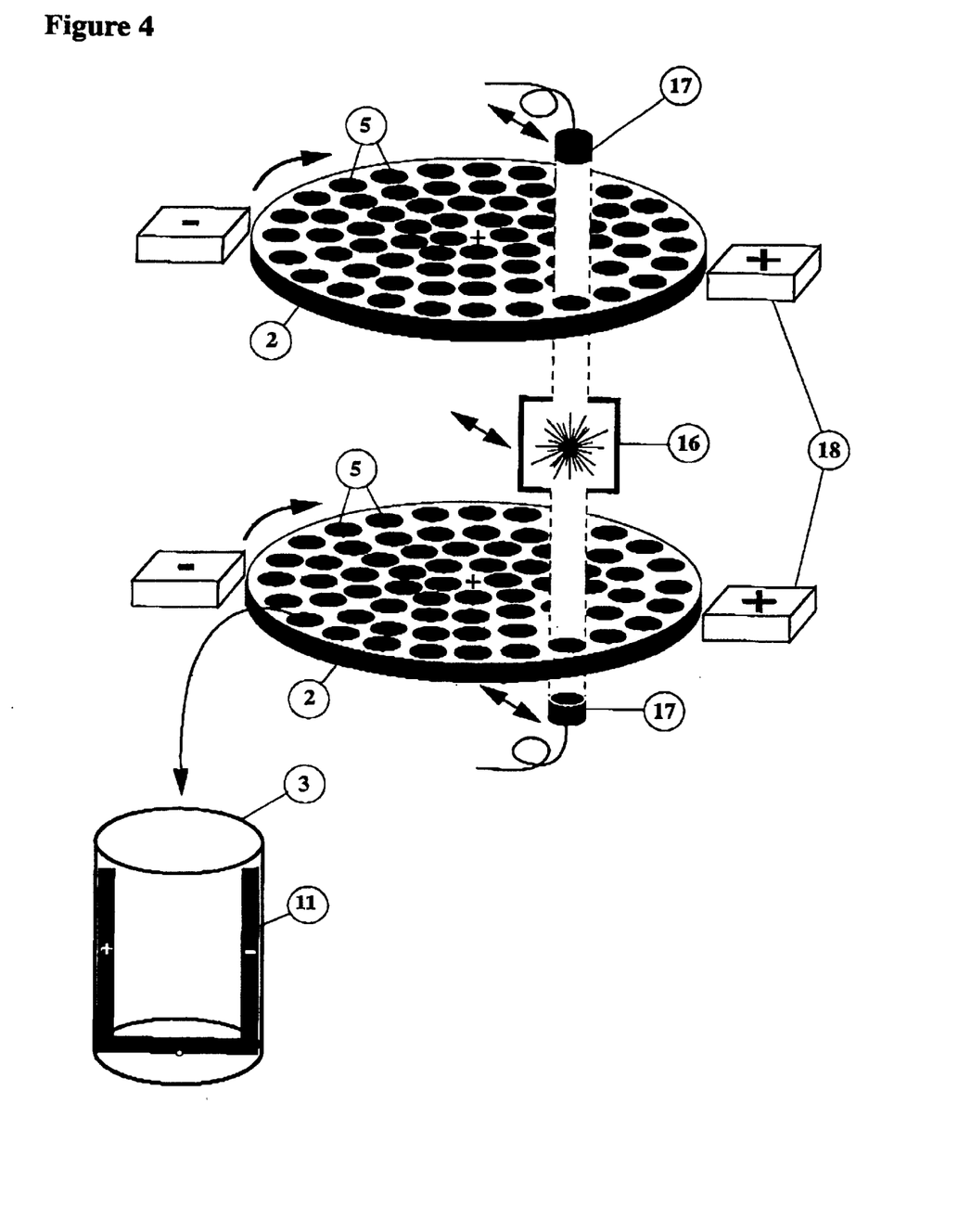
FIG. 4 shows a principle for detecting and monitoring means based on γ-rays and CCD-cameras, and also a magnet mixer rotated by an external magnetic field according to an embodiment of the invention.

In another embodiment, using γ-radiation, as illustrated in FIG. 4, density measurements can be employed to detect the formation of solid particles or structures in a medium or, in general, to detect any density gradient or the presence of phases with different densities. This can be done, for example, by comparing density measurements or pictures of a cell over time. When solid structures are formed, a lower signal value is achieved in the regions with accumulated solids due to the higher density of such structures. This measuring principle can be used to detect the solid formation in a multi-cell system, organized in a geometry as illustrated in FIG. 4 or any other suitable geometry. In FIG. 4, a certain number of cells 5 are organized forming one or more circles in one or two boards 2 rotating at a constant rotation frequency. A γ-source 16 is placed between the rotating boards. The y-rays pass through a collimator and are detected by one or more CCD-detectors 17 placed under and above the rotating boards 2 on in the opposite side of the γ-source. The active area of each detector is also equal to the cell cross sectional area. An external magnetic field 18 rotates the mixer 11. When the boards rotate, each measuring cell will pass in between the γ-source and the detectors, one after the other at a high pace, optionally in many cycles, in order to obtain time resolved information. Density distribution in the cells is measured at each passage and the results are collected sequentially in a matrix giving the basis for the analysis.

The viscosity of a mixture will be affected by the formation of solid structures, such as gas hydrates. The moving velocity of an object with a certain size and shape at a given force field in the medium is a function of the mixture viscosity. FIG. 5 illustrates the application of this principle combined with a method for measurement of the mixer's level or position in the cell. A metal ring 19 is used as a mixer inside the measuring cell. The mixer is pulled up and down using, for example, a magnetic field 22 as illustrated in FIG. 5 The mixer's axial level or position in the cell is measured using two or more detectors 20, 21. When the mixer passes a detector, a pulse of current is measured due to the low resistance of the mixer compared to that of the mixture. Velocity of the mixer is determined by dividing the distance between two neighboring detectors by the measured time delay between two current pulses. Changes in the mixture viscosity are determined by comparing the measured velocities with a set value for the mixture.

Figure 6:
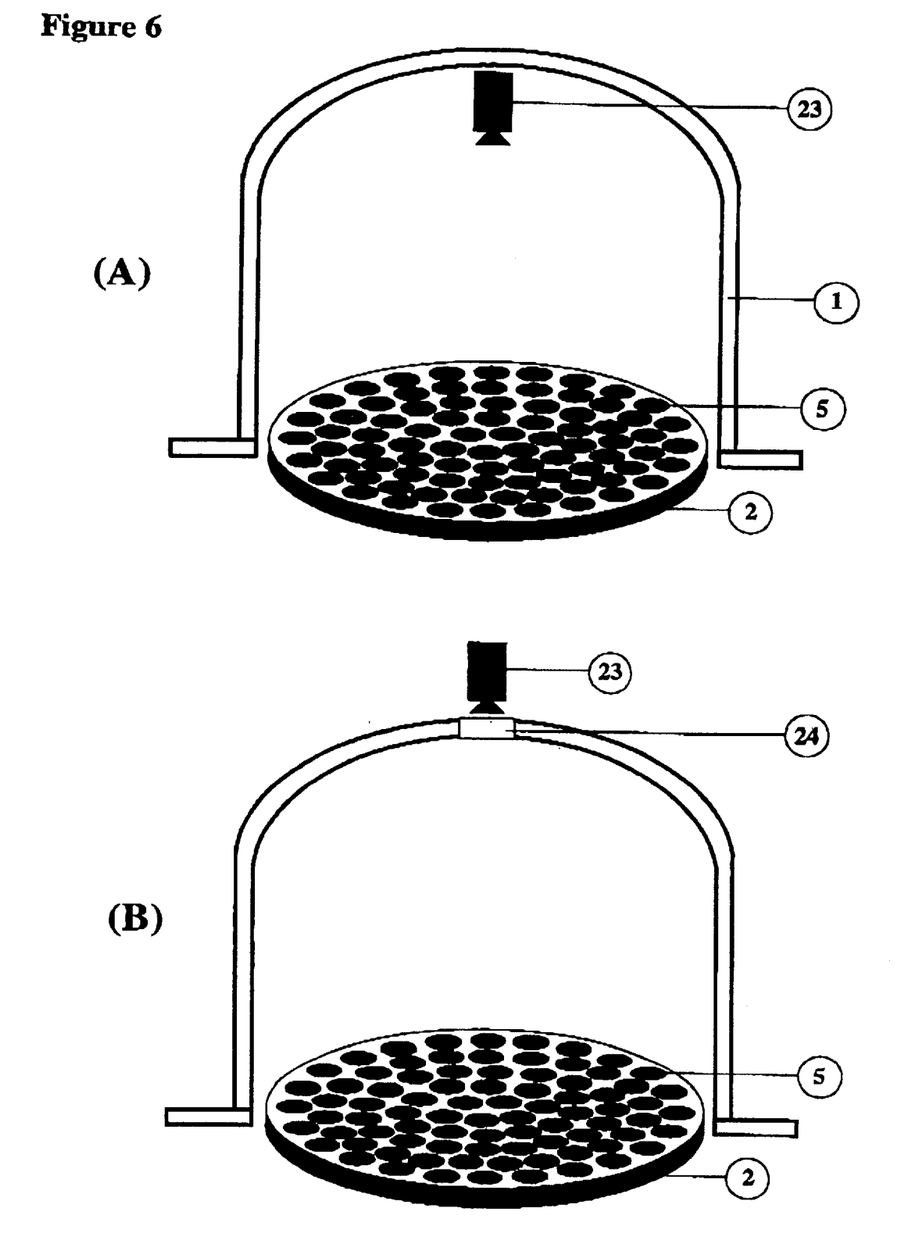
FIG. 6A illustrates a multi test assembly with a camera inside the pressure vessel for detecting the contents in the test cells according to an embodiment of the invention.
FIG. 6B illustrates a multi,test assembly with a camera outside the pressure vessel for detecting the contents in the test cells according to an embodiment of the invention.

If a plate containing cells is open or transparent, any visible contrast appearing in a cell may be surveyed and monitored by the use of one or more video or IR cameras 23, as illustrated in FIGS. 6A and B. The cameras 23 may be mounted inside or outside the pressure vessel through an inspection window 24. Visible contrasts may be obtained in each cell by any suitable means, for example, by using floaters or magnetic stirrers marking viscosity, liquid phase level or temperatures Proper image treatment changes in the cells may be monitored automatically.

The Parallel Data Treatment and Interpretation Unit

The result of the above arrangements is a system containing a certain number of totally separate parallel measuring units with the same measuring conditions such as pressure, temperature and gas mixture feeding. In such system, the measurements are conducted simultaneously or sequentially in all cells. For parallel data treatment and interpretation of the data, any suitable computer and data program may be used. Changes on a test-cell will preferentially be determined by comparing the measured interpretation with a set value for the cell made at the start of the experiment.

Additional advantages of this invention are primarily related to the large rationalization gain, giving a correspondingly large economic saving. The saving is estimated to be 90 to 99%. In other words, either the cost related to a given testing program is reduced by 90–99%, or it is possible within given budget to perform 10–100 or more times as many tests. Such an automated layout will make it possible to perform, for example, 1000 or more tests/experiments simultaneously, and it will thus, be very useful for all research laboratories.

The description of the preferred embodiments given above are to be considered as mere examples of possible designs, and the given measures and other details shall not be considered to be limitations to the invention.

The following examples shall not be considered limiting for the invention and only serve as examples relating to the use of the invention for the detection of gas hydrate formation.

EXAMPLE 1

Figure 7:
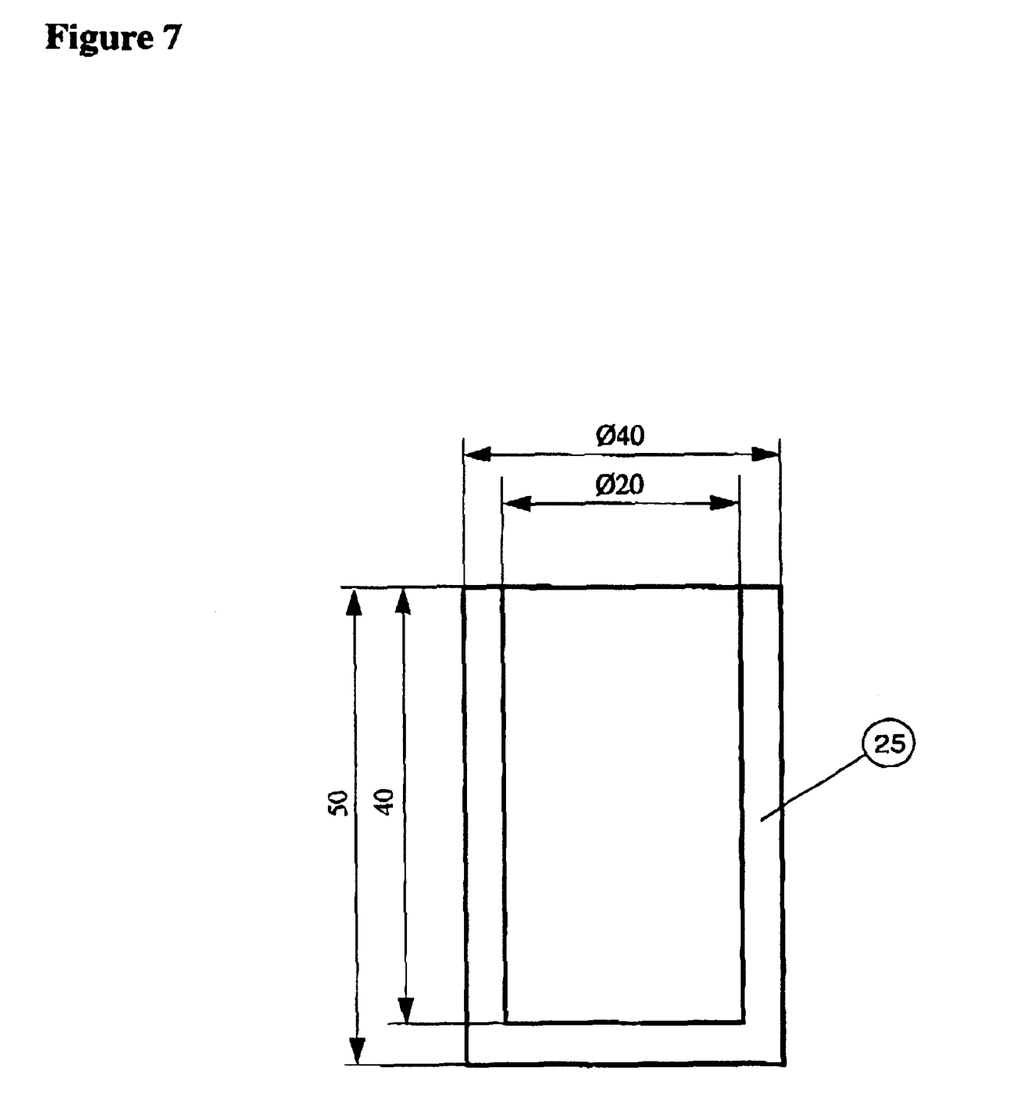
FIG. 7 is a side view of a test cell according to an embodiment of the invention.

One set-up for detection of gas hydrate formation has been carried out in a 10-mm thick-walled aluminum cylinder 25 shown in FIG. 7. The cell 25 is opened at the top with an inner diameter of 20 mm and an inner cell height of 40 mm. The cell was filled with a liquid mixture 27 to be examined. To mix the cell content, a specially designed magnetic mixer 29 was placed in the cell. The rotation frequency of the mixer was chosen and controlled by a magnetic stirrer. In order to cool down the liquid mixture, the cell was placed in a bed of ice-water mixture. The cell temperature was measured by a thermocouple 26 fixed close to the inner side of the cell wall.

An optical probe 12 was inserted into the cell 25 through the cell top opening and was fixed in position by an external support arrangement.

Figure 8:
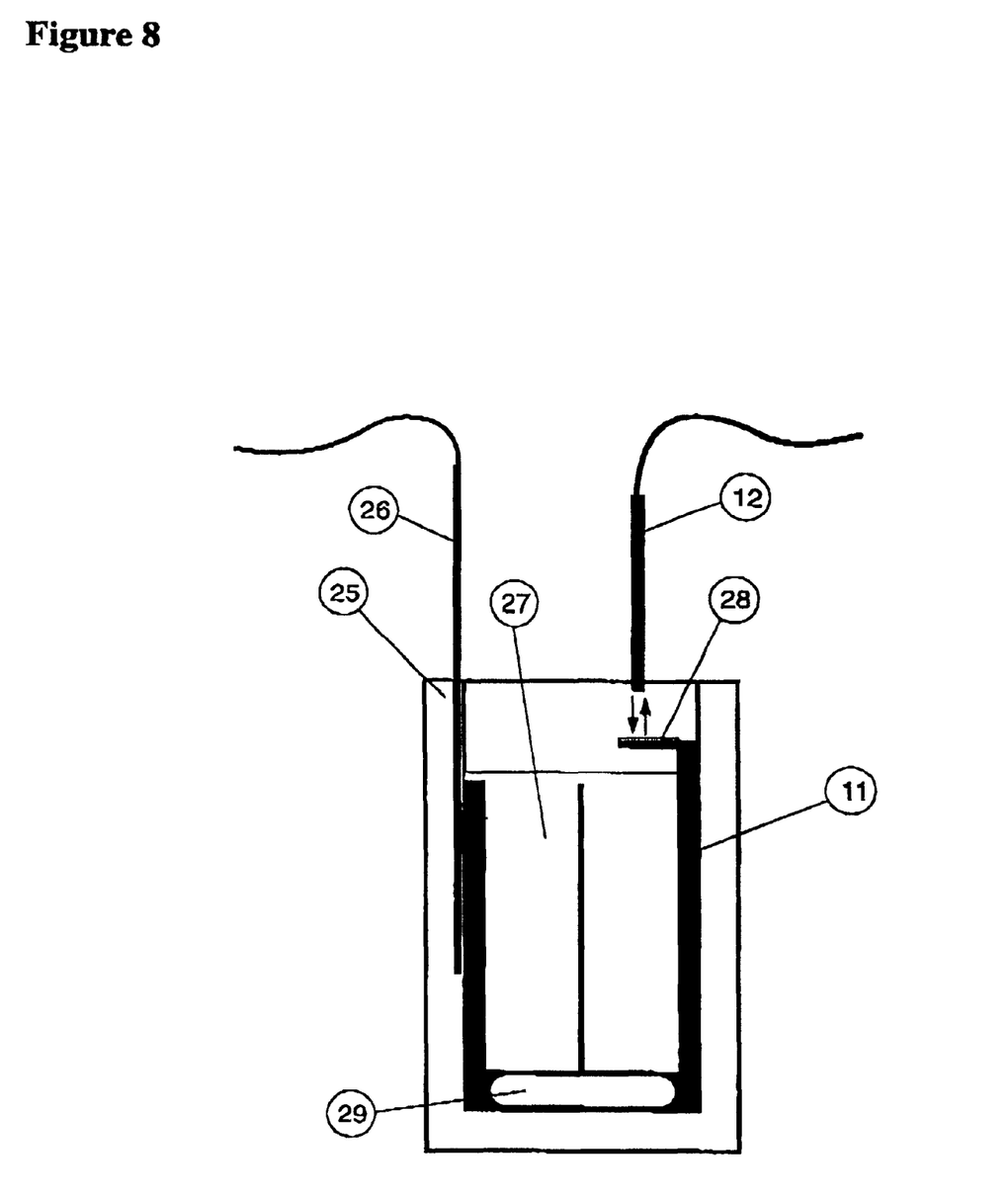
FIG. 8 is a side view of an individual test cell with devices for detecting and monitoring the contents in the test cell according to an embodiment of the invention.

The experiments were done by two different optical methods. One was based on the reflected light from the surface of a handle 28 fixed on one of the mixer blades 11, as shown in FIG. 8. When the handle passes the probe 12, the laser light is reflected from its surface resulting in a considerable increase on the received signal, also seen as a signal spike. The frequency of the detected signal spike corresponds to the rotation frequency of the mixer 29. At constant magnetic field and liquid mixture viscosity, the rotation frequency of the mixer 11 is constant. Any changes in the liquid mixture viscosity at constant magnetic field will affect the mixer rotation frequency. Changes in the mixture viscosity indicate the formation of solid structures such as gas hydrates. One of the advantages of this method is that the reflected laser light from the handle 28 is independent of the liquid mixture color or clearness: This is because the handle is always above the liquid level.

EXAMPLE 2

Figure 9:
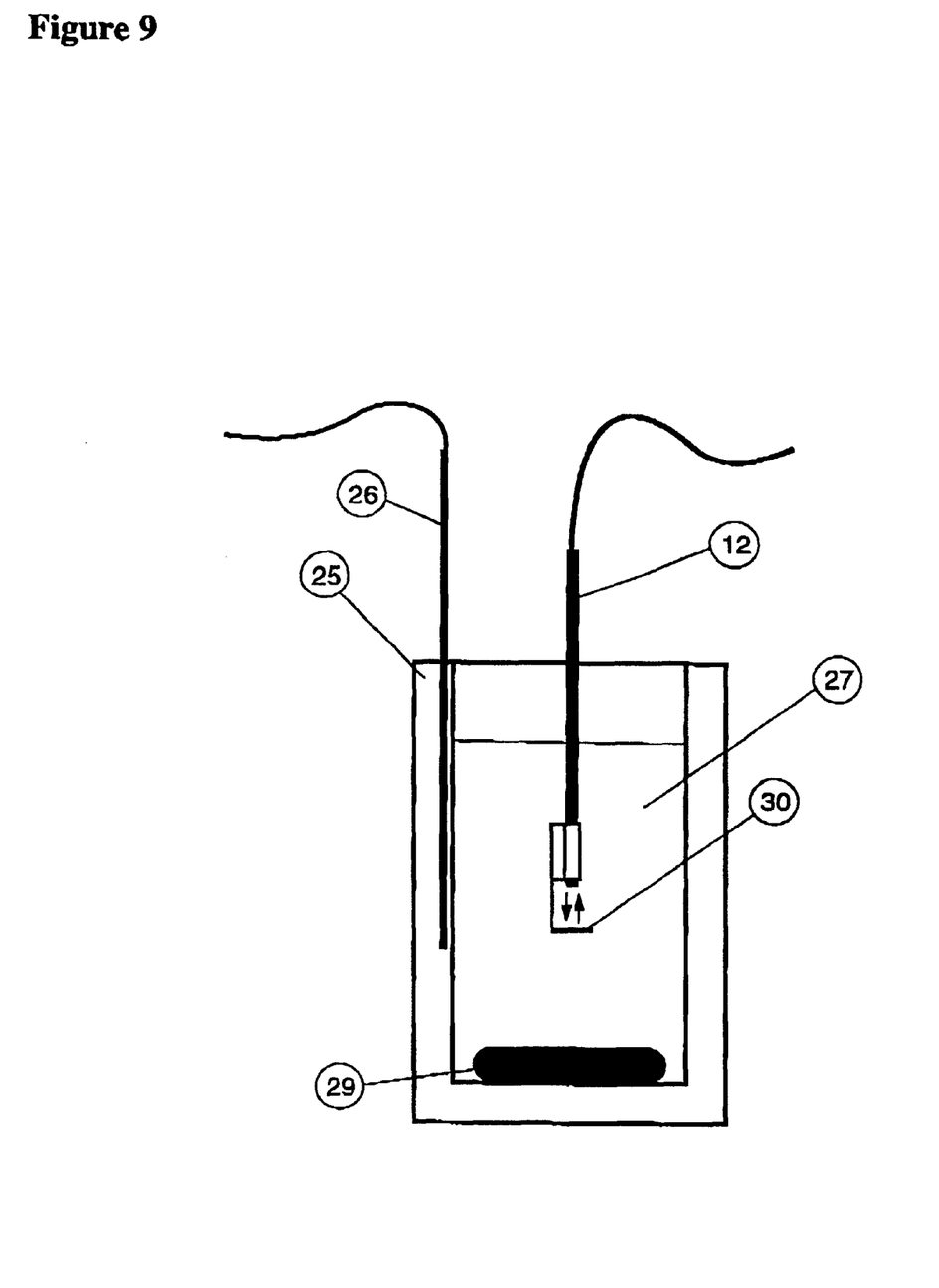
FIG. 9 is a side view of an individual test cell with devices for detecting and monitoring the contents in the test cell according to an embodiment of the invention.

The other method was based on light reflection and attenuation from a mirror or a shining surface 30 placed at a certain distance from the probe tip perpendicular to the probe 12 end surface as shown in FIG. 9. To mix the cell content a magnetic mixer 29 was placed in the cell. The intensity of the received light is a function of the transparency of the medium in between the probe and the mirror. Using this technique, any changes in the liquid mixture 27 transparency indicate the formation of solid structures.

The cell 25 was filled with the liquid mixture 27 at room temperature. The measurements were started with constant mixer rotation frequency. The magnet mixer rotation frequency was kept constant throughout the experiments, at about 500 rotations per minute. Both experiments were done at atmospheric pressure. The experiments were carried out using CC13F-water mixture with a volumetric ratio of 50/50. The same apparatus may be used for elevated pressure systems, when one or more cells are placed in a pressure vessel.

Example 3

Frequency Measurements

Figure 10:
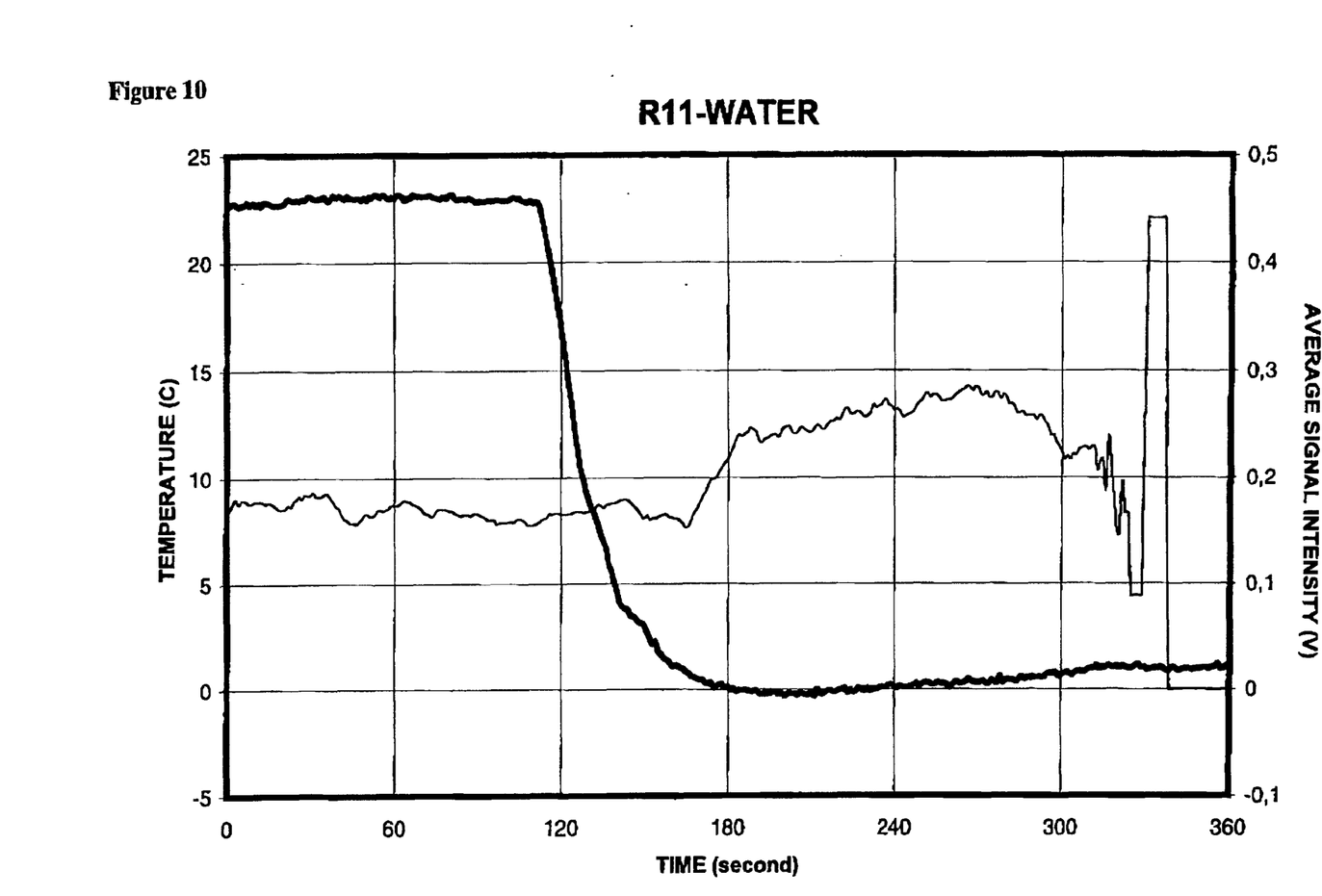
FIG. 10 is a plot of temperature in the test cell and average signal intensity from a probe as a function of time as measured in the system shown in FIG. 8.

A frequency time series measurement was performed generally containing a constant background signal level and a number of signal spikes corresponding to the passage of the handle 28. Since the received signal width and the number of spikes per time unit depends on the rotation frequency of the handle, this method captures any changes in the liquid mixture viscosity or rotation frequency. To interpret the received frequency measurement data, the areas under all curves, which cross a certain set value per time unit were calculated. FIG. 10 shows a histogram of hydrate generation using CCl3F-water mixture based on the calculated average signal values. The left vertical axis indicates the temperature in the cell while the right vertical axis shows the signal contribution from the optical probe. The optical probe collects the reflections from the handle on the mixer indicating the mixture's viscosity. As shown in FIG. 10, in the first 100 seconds, the temperature, which is indicated by the thick line, is constant at about 23° C. The corresponding measurement from the optical probe indicated by the thin-line on the figure also shows a constant mixture viscosity. When the temperature is reduced to about 3° C., a dramatic change in the mixture viscosity, at 170 seconds, is measured indicating the initiation of the hydrate formation. The viscosity increases when at the temperature is about zero, where more hydrates are formed. A slight increase in the temperature profile indicates the heat generation due to hydrate formation. Finally, the last chaotic section in the diagram, at 320 seconds, corresponds to the full hydrate blockage of the cell.

The period of hydrate generation, from the appearance of the first hydrates to the full blockage of the cell is obtained from the same diagram. Such information are also very interesting, for example, for the study of kinetic inhibitors.

Example 4

Concentration Measurements

Figure 11:
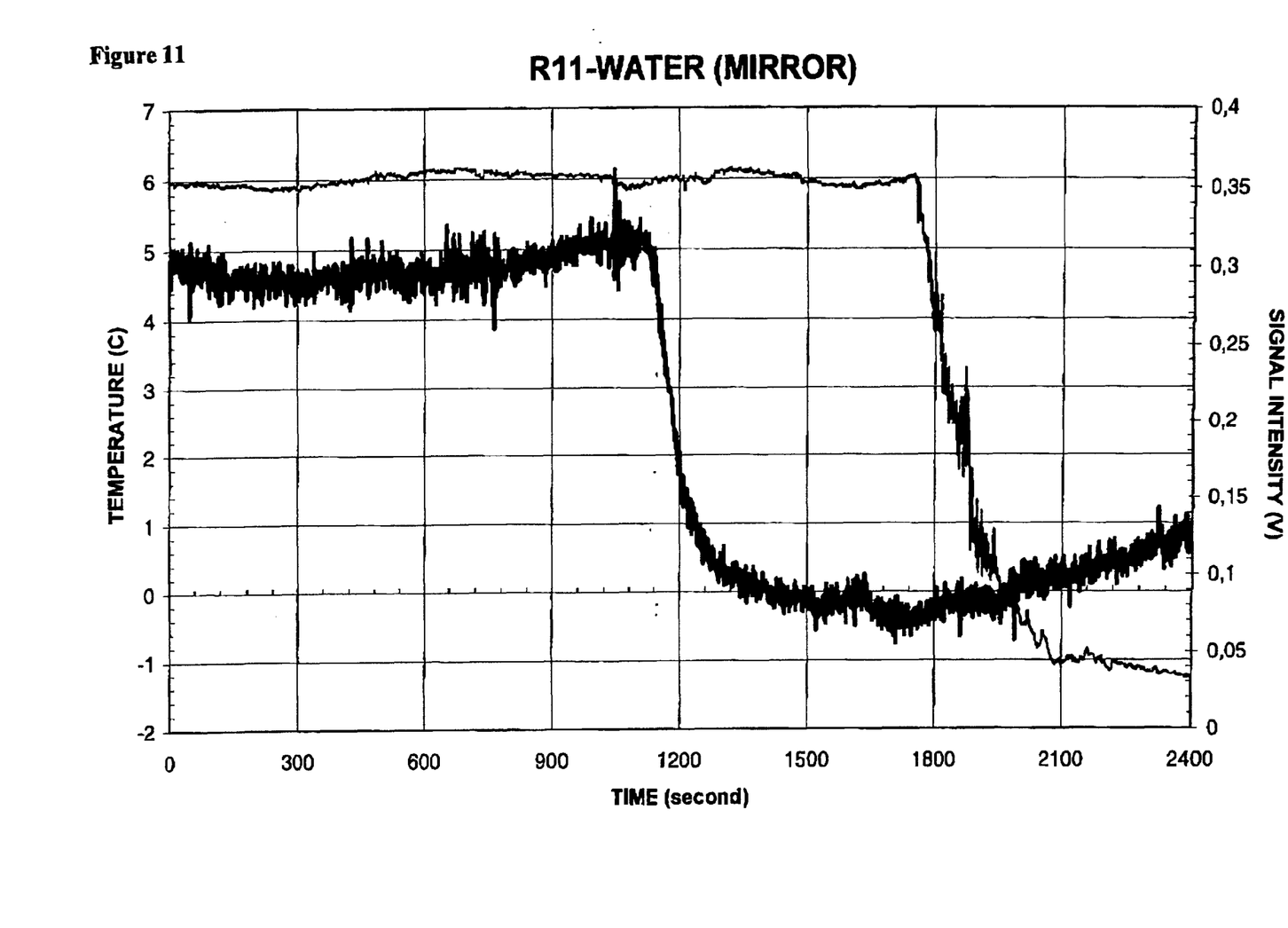
FIG. 11 is a plot of temperature in the test cell and average signal intensity from a probe as a function of time as measured in the system shown in FIG. 9.

The attenuation of light was used to measure the hydrate formation in a setup as described in example 2. As shown in FIG. 11, at a constant temperature about 6° C., the reflected light to the probe is constant. After about 1750 seconds, the temperature is reduced to about zero, and the hydrates start to generate and interact with the light propagating through the solution. This results in the attenuation of the measured reflected light, and can be used to indicate the hydrate formation. It should be noticed that this phenomenon was detected by the probe while the visual observations indicated a transparent liquid mixture. Most of the light was blocked long before the full blockage of the cell. The continued increase in the temperature profile indicates the formation of more hydrate particles that cannot be detected by this method.

The examples above were conducted without elevated pressure, as there are a few systems that can form gas hydrates at 1 bar and at temperatures just above 1° C. The methods can however be used in high pressure systems as they then only require a pressure connection for the fiber cable through the pressure vessel. Each probe is cheap and the number of test cells in the pressure vessel can easily be extended to the number desired. Also, each cell can easily be made with dimensions of 1×2 cm.

Having described preferred embodiments of the invention, it will be apparent to those skilled in the art that other embodiments incorporating the concepts may be used. These and other examples of the invention illustrated above are intended by way of example only and the actual scope of the invention is to be determined from the following claims.

What is claimed is:

1. A multi-test assembly comprising:
   a pressure vessel;
   means for controlling temperature and pressure in said pressure vessel;
   at least one tray or plate arranged inside of said pressure vessel, said at least one tray or plate having a plurality of wells, respectively, organized thereon, said wells constituting test cells;
   an automatic dosing set-up for dosing test samples into said plurality of test cells prior to pressurization of said pressure vessel; and
   detecting and monitoring means for detecting and monitoring contents of each of said plurality of test cells individually in situ.

2. A multi-test assembly according to claim 1, further comprising a disposable insert or lining said plurality of test cells.

3. A multi-test assembly according to claim 1, wherein a degree of interaction between the contents of said plurality of test cells and between said plurality of test cells and an atmosphere in said pressure vessel is controllable.

4. A multi-test assembly according to claim 3, wherein the contents of said plurality of test cells interact fully with the atmosphere in said pressure vessel.

5. A multi-test assembly according to claim 3, wherein there is no interaction between the contents of said plurality of test cells.

6. A multi-test assembly according to claim 1, wherein said detecting and monitoring means comprise a plurality of devices placed on a side of said at least one tray or plate, said plurality of devices being operable to monitor or interact with the contents of said plurality of test cells.

7. A multi-test assembly according to claim 6, further comprising a magnetic stirrer arranged in each of said plurality of test cells, said magnetic stirrers being operable to mix the contents of said plurality of test cells and remove gas bubbles from cell walls of said plurality of test cells.

8. A multi-test assembly according to claim 7, further comprising detector means located outside each of said cell walls of said plurality of test cells, said detector means for sensing movement of said magnetic stirrers inside said plurality of test cells so as to measure viscosities of the contents in said plurality of test cells.

9. A multi-test assembly according to claim 6, wherein said testing and monitoring means comprise optical fiber probes arranged in said plurality of test cells.

10. A multi-test assembly according to claim 6, wherein said testing and monitoring means comprise a γ-source arranged on one side of said at least one tray or plate, and at least one detector arranged on an opposite side of said at least one tray or plate.

11. A multi-test assembly according to claim 6, wherein said testing and monitoring means comprise at least one recording device, wherein said at least one recording device is one of a video camera, an IR camera, and optical fibers operable to observe events in said plurality of test cells simultaneously.

12. A multi-test assembly according to claim 11, wherein each of said plurality of test cells has an appropriate marker arranged therein so as to give visual contrast in an image of said at least one recording device.

13. A multi-test assembly according to claim 11, wherein said at least one recording device is operable to observe at least one of visible reactions and temperature changes in said plurality of test cells, simultaneously.

14. A method for detecting solid structure formation or phase transformation of test samples, said method comprising detecting the solid structure formation or phase transformation using a multi-test assembly comprising a pressure vessel, means for controlling temperature and pressure in the pressure vessel, at least one tray or plate arranged inside of the pressure vessel, the at least one tray or plate having a plurality of test cells organized thereon, means for charging the test samples into the plurality of test cells prior to pressurization of the pressure vessel, and detecting and monitoring means for detecting and monitoring contents of each of the plurality of test cells individually in situ.

15. A method for testing inhibitors for solid structure formation of test samples, said method comprising testing the inhibitors using a multi-test assembly comprising a pressure vessel, means for controlling temperature and pressure in the pressure vessel, at least one tray or plate arranged inside of the pressure vessel, the at least one tray or plate having a plurality of test cells organized thereon, means for charging the test samples into the plurality of test cells prior to pressurization of the pressure vessel, and detecting and monitoring means for detecting and monitoring contents of each of the plurality of test cells individually in situ.

* * * * *